(12) United States Patent
Samuelsson

(10) Patent No.: US 6,783,519 B2
(45) Date of Patent: Aug. 31, 2004

(54) ABSORBENT ARTICLE HAVING MEANS FOR POSITIONING THE ARTICLE IN THE UNDERWEAR OF THE WEARER

(75) Inventor: Ann Samuelsson, Lindome (SE)

(73) Assignee: SCA Hygiene Products AB, Gothenburg (SE)

( * ) Notice: Subject to any disclaimer, the term of this patent is extended or adjusted under 35 U.S.C. 154(b) by 37 days.

(21) Appl. No.: 10/006,365

(22) Filed: Dec. 10, 2001

(65) Prior Publication Data
US 2002/0087132 A1 Jul. 4, 2002

Related U.S. Application Data

(60) Provisional application No. 60/251,872, filed on Dec. 8, 2000.

(51) Int. Cl.[7] ............................................. A61F 13/15
(52) U.S. Cl. ................................ 604/385.05; 604/390
(58) Field of Search ..................... 604/385.01–385.05, 604/389–392, 387

(56) References Cited

U.S. PATENT DOCUMENTS

| | | | | |
|---|---|---|---|---|
| 3,688,771 A | * | 9/1972 | Werner | 604/364 |
| 4,701,178 A | * | 10/1987 | Glaug et al. | 604/387 |
| 4,917,675 A | * | 4/1990 | Taylor et al. | 604/385.02 |
| 5,052,381 A | | 10/1991 | Gilbert et al. | |
| 5,088,993 A | * | 2/1992 | Gaur | 604/385.02 |
| 5,669,898 A | | 9/1997 | Ahr | |
| 6,312,417 B1 | * | 11/2001 | Hansson | 604/385.02 |

FOREIGN PATENT DOCUMENTS

| | | |
|---|---|---|
| EP | 0749742 | 12/1996 |
| SE | 512530 | 3/2000 |
| WO | WO98/20823 | 5/1998 |
| WO | WO00/37015 | 6/2000 |

* cited by examiner

*Primary Examiner*—John J. Calvert
*Assistant Examiner*—Catherine L Anderson
(74) *Attorney, Agent, or Firm*—Young & Thompson

(57) ABSTRACT

An absorbent article such as a sanitary napkin, a panty liner and an incontinence napkin for the absorption of urine or faeces and intended to be carried inside the crotch part of the wearer's underwear, wherein said article has two long sides (15, 16), a first short side (17), a second short side (18), a liquid-permeable casing sheet (3) intended to lie proximal to the wearer in use, a liquid-impermeable casing sheet (2) intended to lie distal from the wearer in use, an absorbent core (4) between said sheets (2, 3), said core comprising one or more layers of material, an adhesive fastener means (6) which functions to affix the article to the wearer's underwear and which is disposed on that side of the liquid-impermeable casing sheet (2) that lies distal from the wearer in use, and a removable protective layer (40) which covers the adhesive fastener means (6) and which has a first short side that faces towards the first short side of said article and a second short side which faces towards the second short side of said article. According to the invention a grip flap (50) is joined to the first short side of the protective layer (40) and extends towards and beyond the second short side of said protective layer on that side of said protective layer (40) which faces away from the liquid-impermeable casing sheet (2).

11 Claims, 4 Drawing Sheets

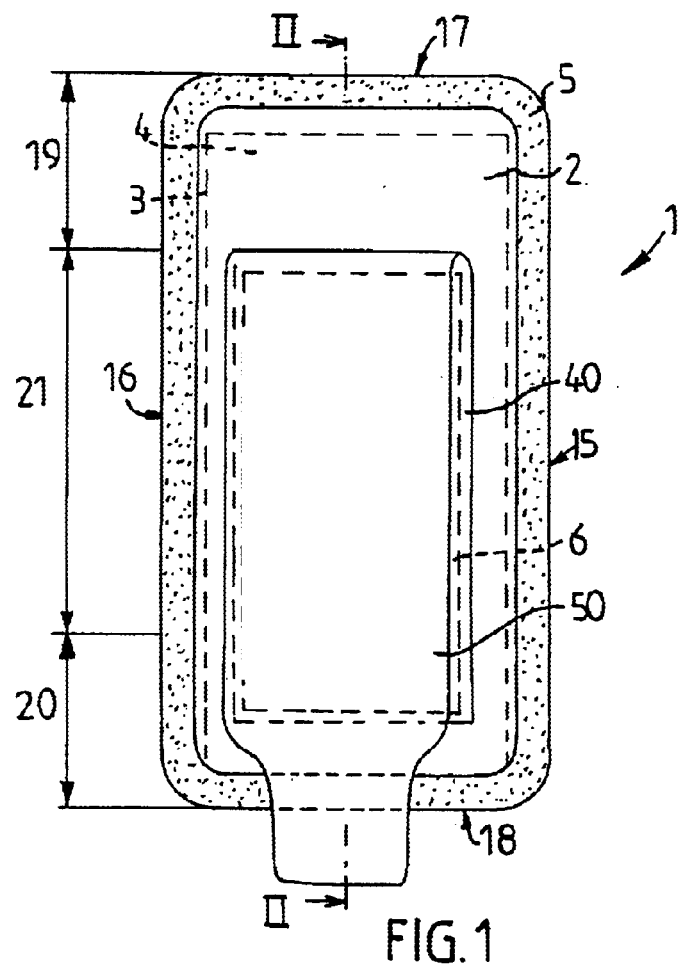
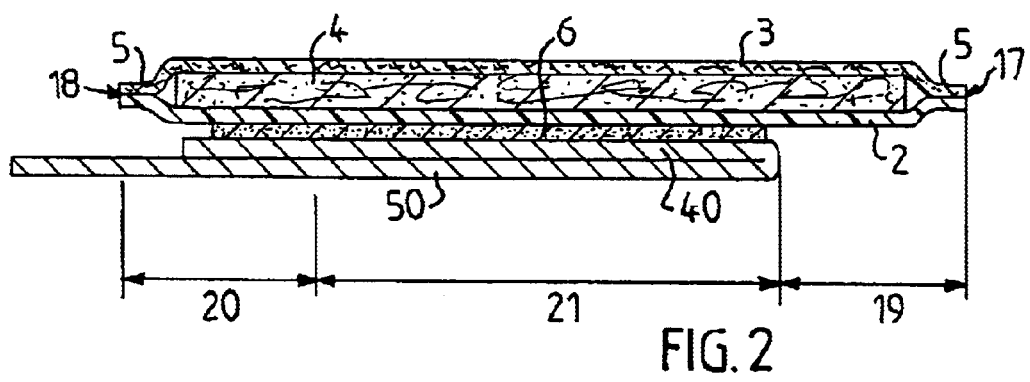

ABSORBENT ARTICLE HAVING MEANS FOR POSITIONING THE ARTICLE IN THE UNDERWEAR OF THE WEARER

FIELD OF INVENTION

The present invention relates to an absorbent article, such as a sanitary napkin, a panty liner, an incontinence napkin for the absorption of urine and excrement or faeces and intended to be carried in the crotch region inside the wearer's underwear, wherein the article has two long sides, a first short side, a second short side, a liquid-permeable casing sheet which is intended to lie proximal to the wearer in use, a liquid-impermeable casing sheet intended to lie distal from the wearer in use, an absorbent core comprising one or more material layers and disposed between said sheets, an adhesive fastener means for fixing the articles in the wearer's underwear and disposed on that side of the liquid-impermeable casing sheet which lies distal from the wearer in use, and a removable protective layer that covers the adhesive fastener device and which has a first short side that faces towards the first short side of the article and a second short side that faces towards the second short side of said article.

DESCRIPTION OF THE BACKGROUND ART

Conventional absorbent articles of the aforesaid kind traditionally have a relatively large surface area, in other words they cover the whole of the crotch region and then often all body orifices of the wearer in that region. A contributory factor to the size of the article is the amount of body liquid or fluid that the article must be capable of absorbing over a determined time period, and also the material from which the article is constructed and its method of construction. The size of the article is also adapted to whether or not it shall be used for the absorption of more than one type of body fluid at one and the same time. Another reason for the size of the article is that it shall present a surface of sufficiently large area to minimise the risk of positioning the article incorrectly in the panties of the wearer. Incorrect positioning of the absorbent article will cause the liquid to land on the edge regions of the article so as to make optimum absorption of liquid into the article impossible, said liquid then either running over said edge regions or failing to land on the article at all, resulting in soiling of the wearer's underwear.

Articles of smaller sizes have been produced in recent times, partly to enhance wearer comfort when using the article, and partly in response to higher user demands for more discrete articles when wearing tightly fitting clothing. It has been possible to reduce the size of such articles with the advent of more effective absorption materials, and the articles have been constructed to fit more closely to the body of the wearer, so as to obtain contact between the article and a wearer's body orifice, which enables the liquid to be absorbed very early in the product, before the liquid is able to run over an excessively large surface. Articles that present a small surface are traditionally panty liners, panty liners adapted for string panties, sanitary napkins that have been given a more body-corresponding format and therewith need not necessarily extend far beyond the body orifice concerned, and inter-labial protectors. Articles that present a three-dimensional surface which is intended to be placed between labia is normally not difficult to position correctly, as the elevation on the upper side of the article is adapted to fit in the labia interspace. Some women, however, prefer a flat absorbent article to the option of carrying a labium protector. When this flat article has a small surface, it is difficult to secure the article in its correct position in the wearer's panties relative to the body outlet orifice. The traditional procedure adopted when using articles that include adhesive fastener devices that are covered with protective layers is to remove the protective layer from the adhesive fastener, direct the article towards the place in the panty which is believed to constitute the correct relationship with the contemplated outlet orifice, and pull up the panties. If the article is felt to be wrongly positioned, the wearer pulls down her panties and repositions the article. This irritates many users. Another drawback that can occur when being forced to reposition the article in the wearer's panties is that the adhesiveness of the fastener device may be impaired by virtue of small fibres having fastened from the panties onto the fastener device so as to impair the adhesiveness of said device, wherewith the article may crinkle and give rise to chafing and irritation of the wearer. In some instances, the adhesiveness of said device may be impaired to such an extent as to prevent fastening of the article, meaning that a new article must be used.

It is known, for instance from WO 96/33683, to use a glue-coated protective device that is adapted to be fastened directly to the body, with the aim of facilitating placing articles in correct positions in relation to a particular body orifice. However, some people question the attachment of articles to their genitals with a skin-adapted adhesive, and are frightened to do so, because they are afraid that this will give rise to a greater degree of enclosure/increased humidity in the region of the article and will be more irritating than articles that include a more traditional fastening system, i.e. articles that include adhesive intended to be fastened to the wearer's panties.

The object of the present invention is to provide an absorbent article of the kind mentioned in the introduction, that can be readily placed in the correct position in the wearer's underwear and that will eliminate the risk of impairment of the adhesiveness of the fastener device in the event of needing to reposition the article in the wearer's underwear.

SUMMARY OF THE INVENTION

This object is achieved with an absorbent article, such as a sanitary napkin, a panty liner, an incontinence napkin for absorbing urine or faeces, which is intended to be worn in the crotch region within the underwear of the wearer, and which includes two long sides, a first short side, a second short side, a liquid-permeable casing sheet intended to lie proximal to the wearer in use, a liquid-impermeable casing sheet intended to lie distal from the wearer in use, an absorbent core disposed between said sheets and including one or more layers of material, an adhesive fastener device which functions to affix the article in said underwear and is disposed on that side of the liquid-impermeable casing sheet that lies distal from the wearer in use, and a removable protective layer which covers the adhesive fastener device and which has a first short side facing towards the short side of the article and a second short side which faces between the second short side of the article, wherein said adhesive article is characterised by a grip flap that is connected to the first short side of said protective layer and which extends towards and beyond the second short side of said protective layer on that side of said layer which faces away from the liquid-impermeable casing sheet. The grip flap enables the user to remove the protective layer when the panties have been almost completely pulled up, which enables the user of the article to determine very easily whether or not the article has been positioned correctly.

In one preferred embodiment of the invention, the grip flap is comprised of an extension of the protective layer. According to another embodiment, the extension of the protective layer comprises a separate part that is fastened to the protective layer at the first short side of said article.

In a further embodiment of the inventive article, said article is, in addition, also provided with a high friction fastener device, for instance a touch-and-close fastener or foamed material, or an adhesive material that has low adhesion. The purpose of this additional fastener device is to enable the article to be secured to the article and held in its correct position in the user's underwear during the time that the user grips the grip flap and pulls the protective layer away from the adhesive fastener device after having pulled up her panties.

BRIEF DESCRIPTION OF THE DRAWINGS

The invention will now be described in more detail with reference to embodiments thereof and also with reference to the accompanying drawings, in which FIG. 1 is a plan view of a panty liner according to a first embodiment, seen from the side which is intended to be fastened to the wearer's underwear;

FIG. 2 is a longitudinal section view of the panty liner shown in FIG. 1, taken on the line II—II in said Figure;

DESCRIPTION OF EMBODIMENTS

Figure 3:
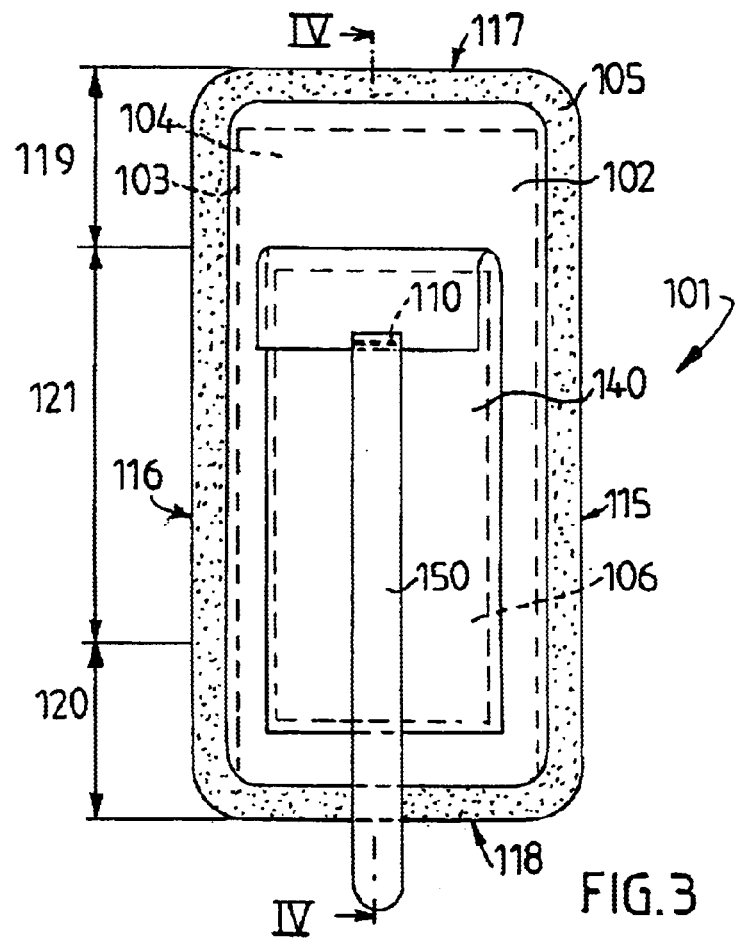
FIG. 3 is a plan view of a second embodiment of a panty liner, seen from the side that is intended to be fastened to the wearer's underwear.

Although the embodiments described below are concerned with an absorbent article in the form of a panty liner, it will be understood that said embodiments may also apply to a sanitary napkin, an incontinence napkin for urine, or a napkin for faeces incontinence.

Shown in FIGS. 1–2 is a panty liner 1 that includes two long sides 15, 16, a first short side 17, a second short side 18, two end portions, and a centre portion 21 located between said end portions. A liquid-permeable casing sheet 3 is disposed on that side of the panty liner 1 which is intended to lie proximal to the wearer in use. The liquid-permeable casing sheet 3 will suitably consist of a soft skin-friendly material. Different types of non-woven materials are examples of suitable liquid-permeable material. Other useable casing sheet materials are perforated plastic film, net, knitted, crotchet or woven textiles and combinations and laminates of these types of material.

The panty liner 1 also includes a liquid-impermeable casing sheet 2 on that side of the panty liner 1 which is intended to lie distal from the wearer in use. The liquid-impermeable casing sheet 2 is typically comprised of thin plastic film. Alternatively, the liquid-impermeable casing sheet may consist of a liquid-permeable material that has been made impervious to liquid in some way or another. In such treatments, the surface may be coated with a glue that is not permeable to liquid, or laminating the liquid-permeable sheet with a liquid-impermeable material, or heat calendering an initially liquid-permeable material so as to melt the surface of said sheet and therewith obtain a liquid-impermeable sheet. Alternatively, there may be used other textiles which consist of hydrophobic fibres and which are so dense that they can be used as a liquid barrier sheet.

The two casing sheets 2, 3 are joined together and form an outwardly projecting connection edge 5 around the contour line of the panty liner. The two sheets may be joined together by any known suitable technique, such as by gluing, welding or sewing.

A fastener means 6 in the form of a longitudinal, rectangular area of adhesive glue is disposed on that surface of the liquid-impermeable casing sheet 2 that lies distal from the wearer in use. The fastener means 6 extends over the major part of the liquid-impermeable casing sheet 2, with the exception of a small limited area in at least one of the regions of the end-parts 19 and 20.

The fastener means 6 is covered by a removable protective layer 40. The protective layer 40 has release properties on at least that side which faces towards the adhesive fastener means 6, so as to protect said means against the presence of dirt and dust, and from preventing the adhesive to adhere to other non-desired surfaces or against itself until the panty liner shall be used. A grip flap 50 is joined to the protective layer 40, said grip flap extending from the protective layer 40 at the first short side 17 and also towards and beyond the second short side 18 on the underside of the protective layer 40, i.e. on that side which faces away from the liquid-impermeable casing sheet 2. In the case of the embodiment illustrated in FIGS. 1 and 2, the grip flap 50 is an extension of the protective layer 40. That part of the grip flap 50 which extends beyond the protective layer 40 provides a readily accessible grip end. The grip end may conveniently also extend beyond the short side 18 of the panty liner.

In the case of the illustrated embodiment, the grip flap 50 has the same width as the protective layer 40, although this is not necessarily so as the flap may, instead, be narrower or wider than the protective layer. Neither need the grip flap be rectangular in shape, but may have a shape which narrows from the short side 17 towards the short side 18.

The grip flap 50 enables the user of the article to remove the protective layer 40 when the wearer's panties have been almost pulled up around the wearer's buttocks, i.e. to a position in which the wearer is able to feel the position of the panty liner against her body with her hand on the outside of her underwear, and hold the panty liner in position while peeling the protective layer 40 away from the adhesive fastener means 6. Peeling of the protective layer successively away from the adhesive surface requires very little force, which means that the panty liner can be easily held in place as the protective layer is removed. The panty liner can be placed with the grip flap facing either forwards or rearwards, depending on the desired placement of the panty liner against the body. If the article is intended to absorb vaginal fluid, it is beneficial, for instance, to place the article in the wearer's panties against her body with the grip flap facing forwards towards the wearer's stomach, whereas if the absorbent article is to be used for absorption of faeces or excrement, the article is positioned so that the grip flap faces rearwards in the crotch region opposite the anus, so that the grip flap will point rearwardly towards the wearer's back.

Located between the casing sheet 2, 3 is a thin flexible absorbent core 4, which may include one or more layers of material. Cellulose pulp may be a suitable absorbent core material. This material may be kept in rolls, bales or sheets which are dry-defibred and converted in a fluffed state to a pulp mat, sometimes with an admixture of superabsorbents, which are polymers that are capable of absorbing several times their own weight of water or body fluid. Examples of other useable materials are different types of foamed material, for instance compressed foamed material or regenerated cellulose, e.g. viscose known from SE 9903070-2, natural fibres such as cotton fibres, peat, or the like. It is, of course, also possible to use absorbent synthetic fibres, or mixtures of natural fibres and synthetic fibres.

Figure 4:
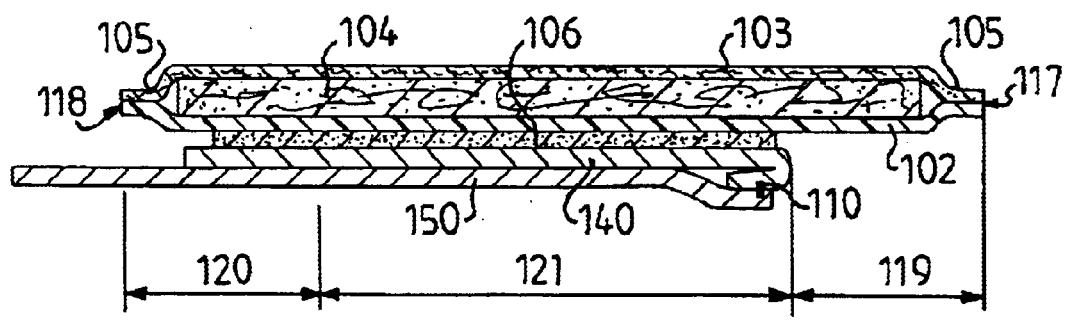
FIG. 4 is a longitudinal section view of the panty liner shown in FIG. 3, taken on the line IV—IV in said Figure.

FIGS. 3 and 4 illustrate a second embodiment of the panty liner and show a panty liner 101 of essentially the same construction as the panty liner 1 shown in FIGS. 1 and 2. The reference numerals used to identify the various parts of the panty liner in FIG. 3 are therefore analogous with the reference numerals used to identify the components of the panty liner shown in FIGS. 1 and 2, although with the addition of 100. The panty liner of FIGS. 3 and 4 differ from that of FIGS. 1 and 2 in so much that the grip flap 150 is comprised of separate material that has been fastened to the protective layer 140 with a join 110. The join 110 between the protective layer 140 and the grip flap 150 may, for instance, be made with the aid of an adhesive medium, or by fusing the materials together by hot rolling or by ultrasound or by riveting.

Figure 5:
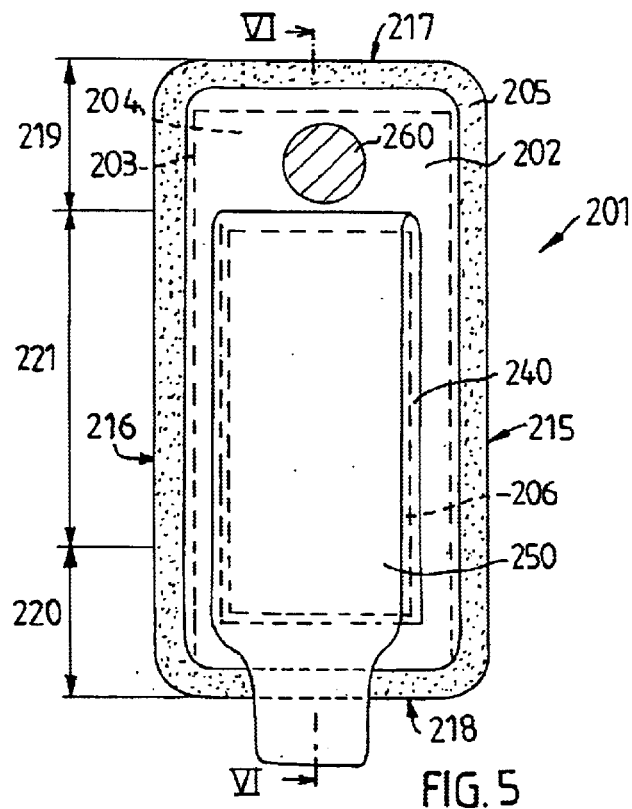
FIG. 5 is a plan view of a third embodiment of a panty liner, seen from the side that is intended to be fastened to the wearer's underwear.
Figure 6:
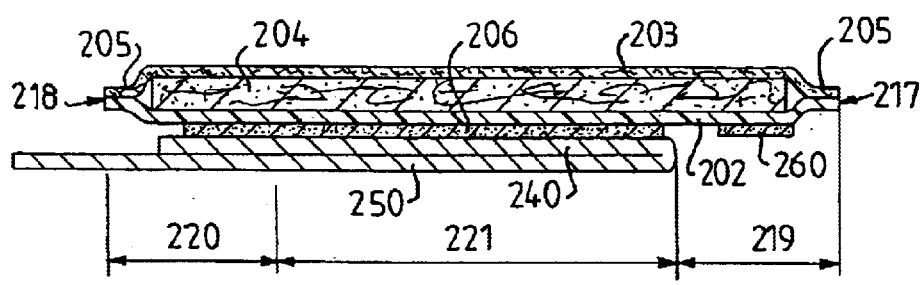
FIG. 6 is a longitudinal section view of the panty liner shown in FIG. 5, taken on the line VI—VI in said Figure.

FIGS. 5 and 6 illustrate a further variant of a panty liner of essentially the same construction as the panty liner 1 shown in FIGS. 1 and 2. Consequently, the different components of the panty liner shown in FIGS. 4 and 5 have been identified with the same reference numerals as those used to identify the components of the panty liner shown in FIGS. 1 and 2, although with the addition of 200. The difference between the panty liner shown in FIGS. 5 and 6 and the panty liner shown in FIGS. 1 and 2 reside in the provision of an additional fastener means 260 placed in the end-part that lacks adhesive fastener means 206. This additional fastener means 260 may consist in a high friction device, such as touch-and-close material, foamed material or adhesive material that has low adhesion. By low adhesion of the adhesive material is meant that the force required to peel or pull the article with the adhesive material from a cotton surface (the quality of the cotton shall illustrate the quality of the panties or underpants) shall be between 1.0–1.9 Newtons. This force is measured with standardised equipment designated Instron 1122, 4301 or 4464, said equipment being connected to a printer.

The test samples are prepared by placing a panty liner provided with said fastener means 260 against a cotton material and fastening said material by rolling a 2 kilogram heavy and 50 mm wide metal roller over the materials at a speed of 1500 mm/min. in one cycle. The sample is placed in the test apparatus, by fastening one end-part of the material layer in an upper clamp or clip and fastening the other material part in a bottom clamp or clip. The measuring process is carried out at a temperature of 23° C. and 50% relative humidity at a tensile speed of 500 mm/min., a pulling length that corresponds to the adhesive surface of the sample, and that the test sample is angled at 90° in relation to the pulling direction. The force is measured in Newtons (N).

Figure 7:
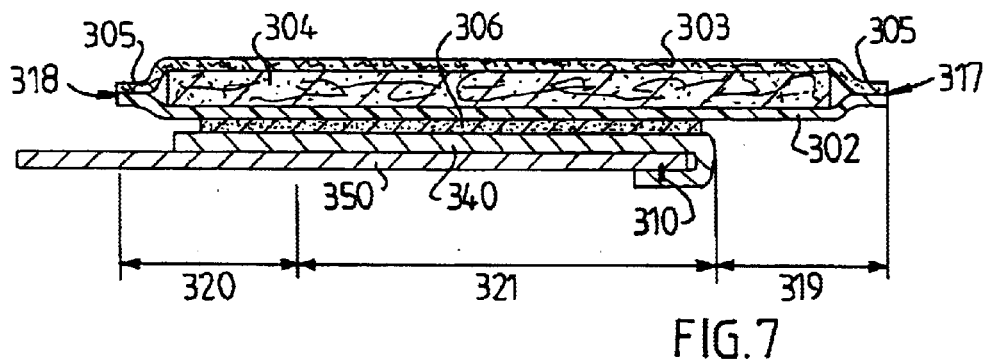
FIGS. 7–9 show respective examples of how grip flaps comprised of material other than the protective layer material can be fastened to said protective layer.
Figure 8:
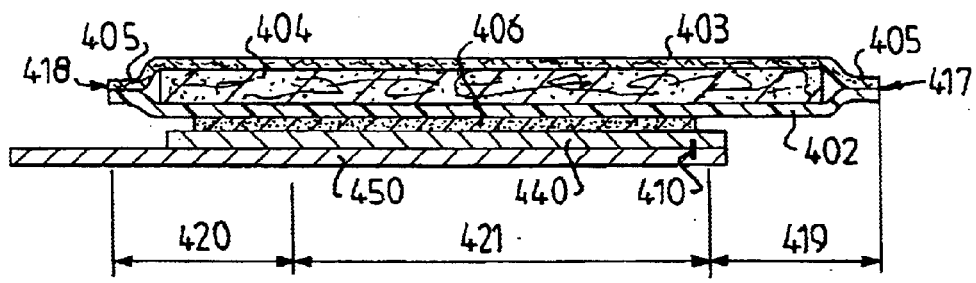
Figure 9:
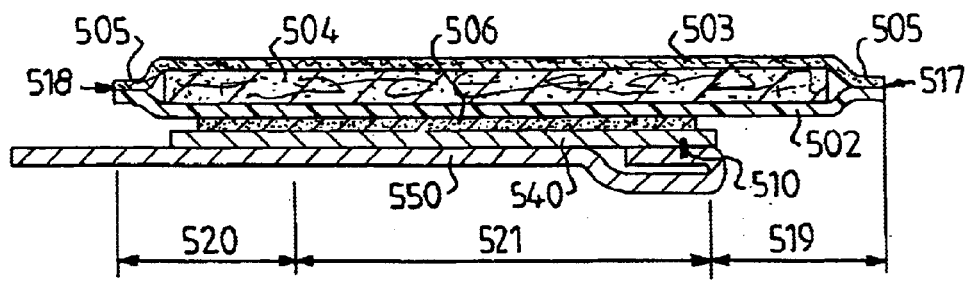

FIGS. 7–9 illustrate examples of how grip flaps that comprise material other than protective layer material can be joined to one another.

FIG. 7 illustrates an end-part of the protective layer 340 folded over the grip flap 350 and fastened thereto, which means that the join 310 will not extend into that part of the protective layer 340 that lies against the adhesive fastener means 306.

In the FIG. 8 embodiment, neither the grip flap 450 nor the protective layer 440 are folded, but are fastened together at their end-parts which face towards the short side 417.

In the case of the FIG. 9 embodiment, the end-part of the grip flap 550 facing towards the short side 517 is folded double and the inwardly folded end-part is fastened to the protective layer 540 with a join 510.

It will be understood that the invention is not restricted to the illustrated and described embodiments and that all conceivable combinations and variations of said embodiments are encompassed by the accompanying claims.

What is claimed is:

1. An absorbent article selected from the group consisting of a sanitary napkin, a panty liner and an incontinence napkin for the absorption of urine or faeces and intended to be carried inside the crotch part of a wearer's underwear, the article comprising:

two long sides;

a first short side;

a second short side;

two end parts;

a central part located between said end parts;

a liquid-permeable casing sheet intended to lie proximal to the wearer in use;

a liquid-impermeable casing sheet intended to lie distal from the wearer in use;

an absorbent core between said sheets; said core comprising one or more layers of material;

an adhesive fastener means which functions to affix the article to the wearer's underwear, and which is disposed on a side of the liquid-impermeable casing sheet that lies distal from the wearer in use;

a removable protective layer which covers the adhesive fastener means, and which has a first short side that faces towards the first short side of said article, and a second short side which faces towards the second short side of said article; and a grip flap joined to the first short side of the protective layer for facilitating removal of the protective layer; said grip flap extending towards and beyond the second short side of said protective layer on a side of said protective layer which faces away from the liquid-impermeable casing sheet.

2. The absorbent article according to claim 1, wherein the grip flap is an extension of the protective layer.

3. The absorbent article according to claim 1, wherein the grip flap is a separate part that is affixed to the protective layer at the first short side of said protective layer facing towards the first short side of said article.

4. The absorbent article according to claim 1, further comprising a further fastener means disposed on the side of the liquid-impermeable casing sheet that lies distal from the wearer in use.

5. The absorbent article according to claim 4, wherein said further fastener means is placed in one of the end parts of said article.

6. The absorbent article according to claim 4, wherein the further fastener means is made of a high friction material.

7. The absorbent article according to claim 6, wherein the high friction material comprises a foam material or a touch-and-close material.

8. The absorbent article according to claim 4, wherein the further fastener means is made of an adhesive material that has low adhesion.

9. The absorbent article according to claim 5, wherein the further fastener means is made of a high friction material.

10. The absorbent article according to claim 9, wherein the high friction material comprises a foam material or a touch-and-close material.

11. The absorbent article according to claim 5, wherein the further fastener means is made of an adhesive material that has low adhesion.

* * * * *